United States Patent [19]

Norman

[11] Patent Number: 5,794,715

[45] Date of Patent: Aug. 18, 1998

[54] ROTARY TOOL HEAD

[75] Inventor: Gerould W. Norman, Clearwater, Fla.

[73] Assignee: Linvatec Corporation, Largo, Fla.

[21] Appl. No.: 676,759

[22] Filed: Jul. 8, 1996

[51] Int. Cl.$^6$ .................................................. A61B 17/56
[52] U.S. Cl. .................. 173/104; 173/171; 81/436; 606/103
[58] Field of Search .................. 227/19; 173/104, 173/171; 81/436; 606/103, 180, 53

[56] References Cited

U.S. PATENT DOCUMENTS

| | | | |
|---|---|---|---|
| 2,193,477 | 3/1940 | Vellier | 81/436 |
| 3,997,053 | 12/1976 | Bondhus | 206/377 |
| 4,091,880 | 5/1978 | Troutner et al. | 173/163 |
| 4,246,811 | 1/1981 | Bondhus et al. | 81/436 |
| 4,269,246 | 5/1981 | Larson et al. | 81/460 |
| 4,338,835 | 7/1982 | Simons | 81/436 |
| 4,503,737 | 3/1985 | DiGiovanni | 81/436 |
| 4,834,092 | 5/1989 | Alexson et al. | 128/303 R |
| 5,019,080 | 5/1991 | Hemer | 606/73 |
| 5,207,132 | 5/1993 | Goss et al. | 81/460 |
| 5,251,521 | 10/1993 | Burda et al. | 81/460 |
| 5,279,190 | 1/1994 | Goss et al. | 81/460 |
| 5,313,680 | 5/1994 | Ringler | 7/138 |
| 5,380,333 | 1/1995 | Meloul et al. | 606/80 |
| 5,387,217 | 2/1995 | Sefcik et al. | 606/103 |
| 5,431,659 | 7/1995 | Ross, Jr. et al. | 606/103 |
| 5,439,005 | 8/1995 | Vaughn | 128/755 |
| 5,490,860 | 2/1996 | Middle et al. | 606/171 |

OTHER PUBLICATIONS

Literature—The Sodem Power System—National Medical Specialty Inc.—c1994.

*Primary Examiner*—Scott A. Smith
*Attorney, Agent, or Firm*—Cary Reeves; Gene Warzecha

[57] ABSTRACT

An improved rotary tool head includes a modular embodiment having a shaft with a tapered insertion end to ease insertion into a handpiece socket and to cause self-alignment of the shaft with the socket. Another embodiment of the improved rotary tool head includes a collet with nonlinear slots separating the collet tangs. The nonlinear slots cause a wire or shaft inserted into the collet to be centralized in the collet and prevent the wire or shaft from protruding between the tangs.

11 Claims, 6 Drawing Sheets

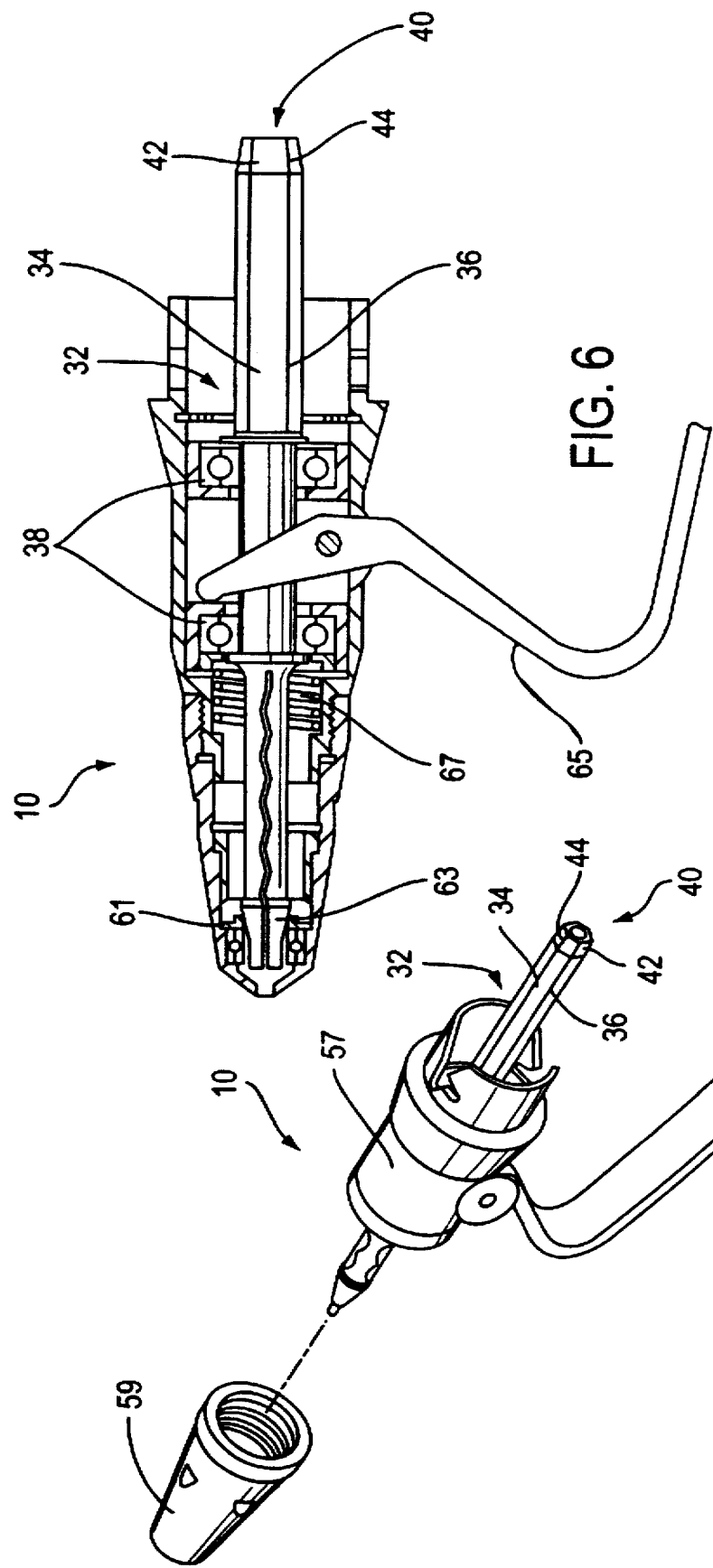

0
ROTARY TOOL HEAD

BACKGROUND OF THE INVENTION

The present invention relates to improvements to a rotary tool head for use with a rotary drive handpiece. The present invention has particular application to modular tool heads and tool heads containing collets such as a surgical wire driver.

Rotary tool heads are used with rotary drive handpieces in many applications such as driving screws and other fasteners, drilling holes, reaming cavities, driving wires and pins, and grinding and shaping. Traditionally, each of these different functions has been performed by a different dedicated handpiece incorporating a specific tool head configuration. In order to save cost and space, some investigators have provided universal handpieces with modular tool heads. Different tool heads, each configured for a different purpose, are releasably mated to the universal handpiece as needed to perform a specific function. Modular tool heads have particular applicability for surgical instruments because of their space and cost saving aspects. The ease of attaching and releasing the modular tool heads is important to the user. One problem that occurs when attaching a modular tool head is shaft misalignment. In many prior art modular tool heads, shaft misalignment can cause frustration and loss of time and concentration as the shaft is manually realigned to ensure proper engagement. This problem is worsened in modular tool heads, such as some wire driver configurations, that have free wheeling shafts that are not gripped by the user during attachment of the tool head. With free wheeling shafts, if the shaft is misaligned, turning the tool head back and forth while the insertion end of the shaft is in contact with the handpiece does not tend to align the shaft with the socket because the shaft bearings allow the shaft to turn within the tool head.

Also, many rotary tool heads contain collets for gripping a shaft or wire. Collets are used in rotary tool heads for holding grinding burrs and for gripping pins and wires. A surgical wire driver is one such application that includes a collet for gripping a wire. The collet has a longitudinal axis that is in alignment with a cannula extending through the wire driver and handpiece. The cannula allows for the use of wire longer than the collet itself since the wire can extend completely through the instrument. The wire must be loaded into the collet and cannula prior to use. It is important to the user that the wire is easily loadable into the collet and that the wire is loaded in proper alignment with the collet axis. A prior art shaft and collet assembly is shown in FIG. 1. The assembly includes a shaft 1 having a collet end 3. The shaft is mounted in bearings 4 for free rotation. This assembly is then mounted in a tool head housing. The collet end 3 includes tangs 5 parallel to the longitudinal axis. The tangs 5 are separated by linear slots 6. In these prior art collets, a wire 7 can exit the grooves between the collet tangs and miss going into the cannula as shown in FIG. 1. When this happens, the wire must be withdrawn and reinserted. This procedure can be frustrating and time consuming. In addition, if a portion of the wire slips into and is gripped in one of the grooves between the tangs, the wire will be off axis and the wire will not run true as the user tries to drive it. Similarly, in a collet used for gripping a grinding burr, the burr must be aligned with the collet axis or the burr will not spin true.

SUMMARY OF THE INVENTION

The present invention provides improvements for rotary tool heads. In the case of a modular tool head, the shaft is provided with a polygonal cross section for transmitting rotary motion. The shaft is insertable into a socket having a corresponding polygonal shape in the handpiece. The end of the shaft is tapered to ease insertion. Planar surfaces corresponding to each side of the shaft polygon converge toward the end of the shaft. In this way, the corners of the polygon continue along the tapered portion as its cross sectional area decreases. When the shaft is inserted into the socket, the taper allows the shaft to start into the socket. Once started, the corners of the tapered shaft strike the flats of the socket. Because the end is tapered and the corners of the polygon extend along the tapered portion, the force of the socket flats on the corners of the tapered portion cause the shaft and socket to rotate into alignment with one another. The self aligning nature of this arrangement results in an easily attachable tool head.

The present invention also prevents misalignment of wires or shafts placed in a collet by providing a collet in which the tangs are separated by nonlinear grooves. Examples include zig-zag and spiral grooves. With the grooves being nonlinear, the wire or shaft cannot exit between the tangs. The wire or shaft is guided down the middle of the shaft between the tangs and the wire or shaft is centralized in the collet and runs true.

BRIEF DESCRIPTION OF THE DRAWINGS

FIG. 5 is a partially exploded perspective view of the rotary tool head of FIG. 4.

FIG. 6 is a front sectional view of the rotary tool head of FIG. 4.

DETAILED DESCRIPTION OF THE INVENTION

Figure 1:
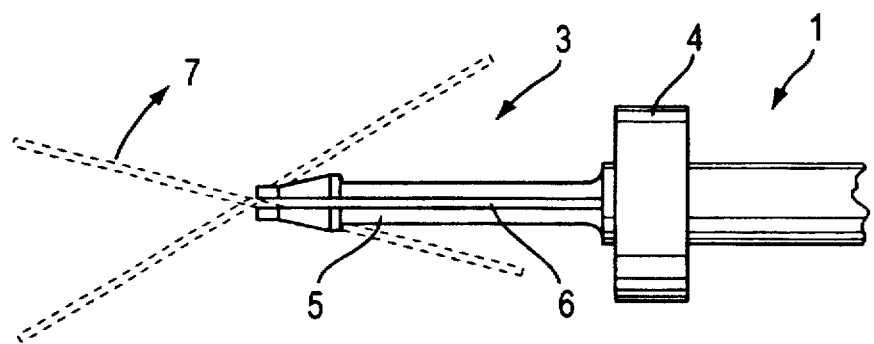
FIG. 1 is a side plan view of a prior art shaft assembly.
Figure 4:
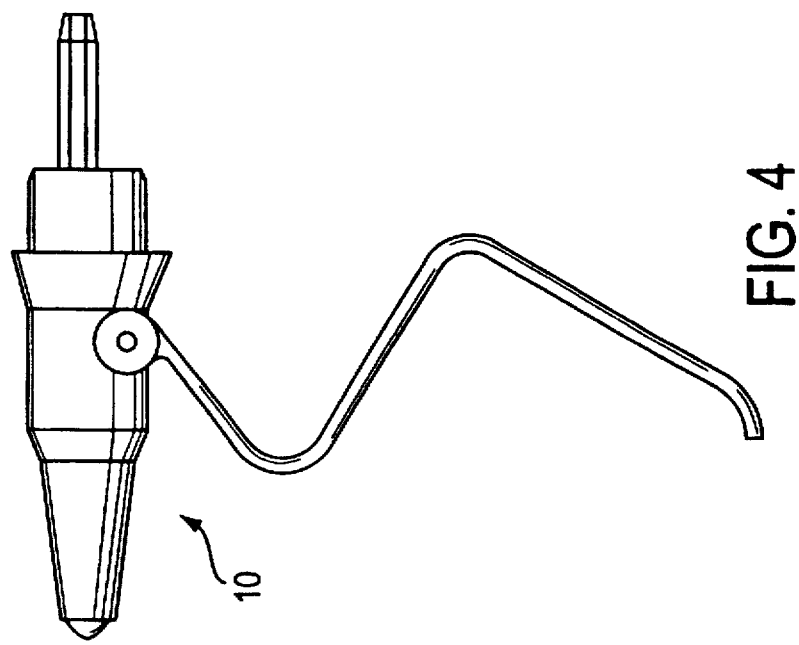
FIG. 4 is a front plan view of a rotary tool head according to the present invention.
Figure 3:
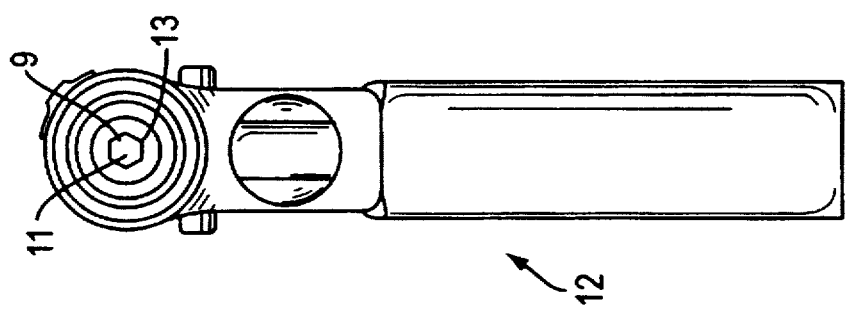
FIG. 3 is a side plan view of the rotary handpiece of FIG. 2.
Figure 2:
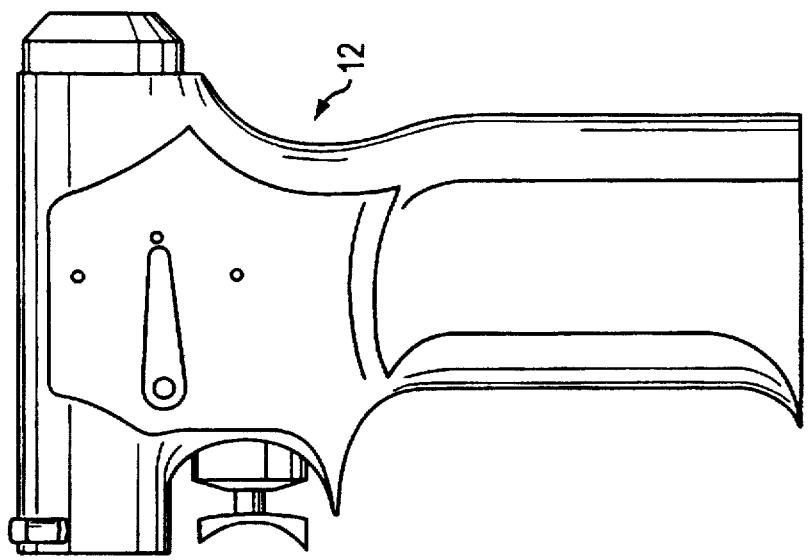
FIG. 2 is a front plan view of a rotary handpiece according to the present invention.

FIGS. 2–6 depict an exemplary modular tool head 10 and rotary handpiece 12 through which the various aspects of the present invention will be described. The particular tool head shown is a modular orthopaedic wire driver that is releasably engageable with the handpiece. The handpiece 12 includes a polygonal socket 11 for matingly engaging a drive shaft on the tool head 10. The socket 11 includes a plurality of sides 9 with adjacent sides meeting at corners 13. Functionally different tool heads and non-modular tool heads may also incorporate the present invention as will be described.

Figure 7:
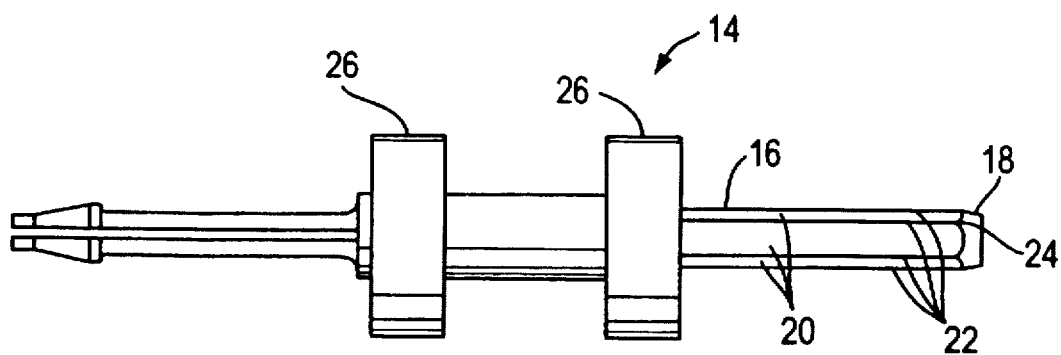
FIG. 7 is a front plan view of an embodiment of a shaft assembly.
Figure 8:
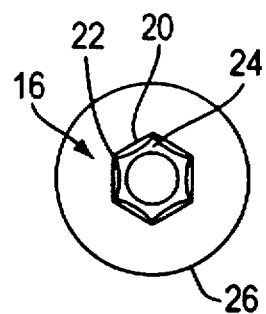
FIG. 8 is a side plan view of the shaft assembly of FIG. 7.
Figure 9:
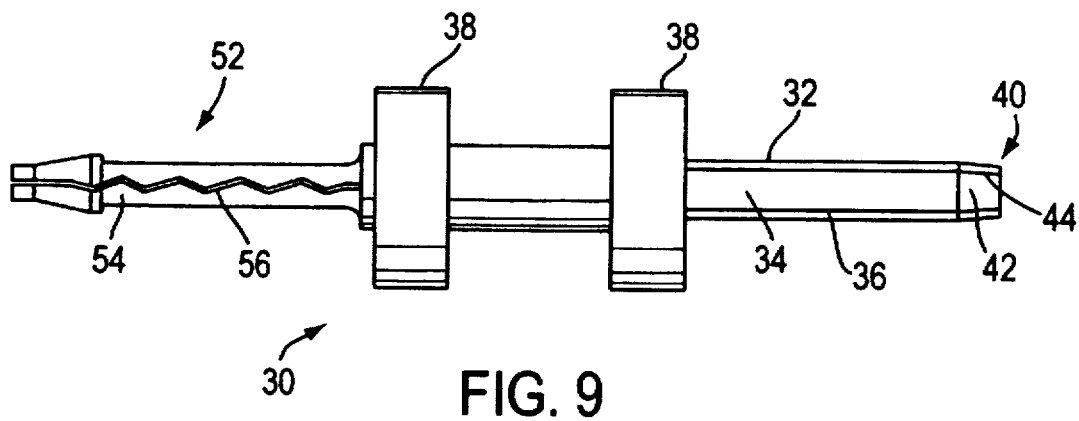
FIG. 9 is a front plan view of an alternative embodiment of a shaft assembly.
Figure 10:
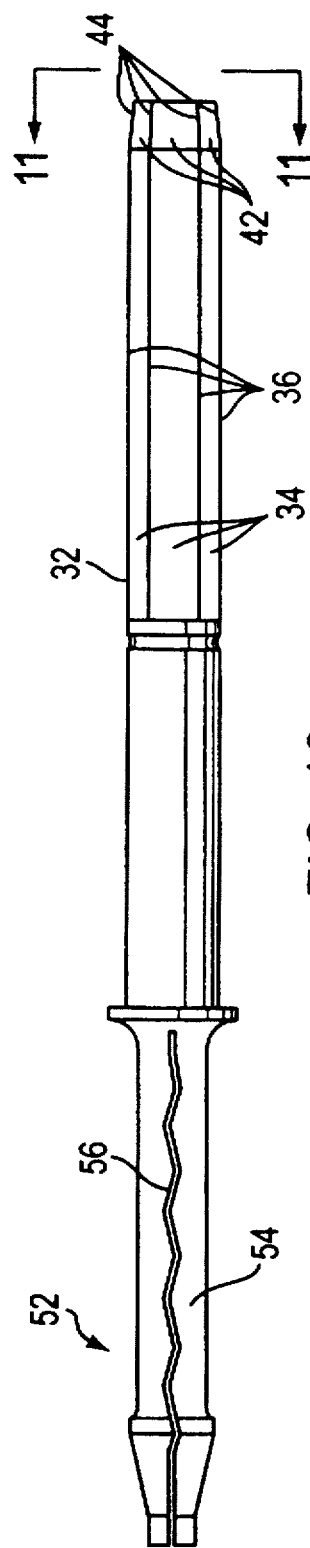
FIG. 10 is a front plan view of the shaft of the shaft assembly of FIG. 9.
Figure 11:
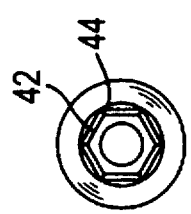
FIG. 11 is a side plan view of the shaft of FIG. 10.
Figure 12:
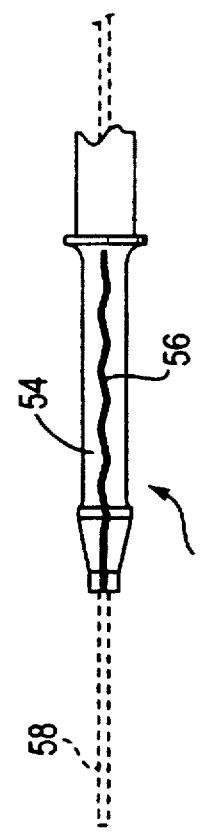
FIG. 12 is a front plan view of the collet end of the shaft of FIG. 10.

FIGS. 7 and 8 depict an embodiment of a tool head shaft assembly 14 having a shaft 16 with a tapered insertion end 18. The shaft 16 has a polygonal cross sectional shape perpendicular to its longitudinal axis. The shaft includes a plurality of sides 20 with adjacent sides meeting at corners 22. The shape of the shaft 16 corresponds to the socket 11 so that they positively engage to transmit torque. The exemplary shaft 16 and socket 11 have a hexagonal shape. The insertion end 18 is ground to a frustoconical taper that blends with the hex-shaped shaft 16. In use, the frustoconical insertion end 18 is inserted into the polygonal socket 11. As the end 18 is brought into general alignment with the socket 11, the taper guides the end 18 into the socket 11 thus easing attachment of the head 10 to the handpiece 12. However, it was found that the frustoconical shape of the end 18, allows the end 18 to sometimes bind in the socket 11. This happens when the transition regions 24 from the frustoconical end 18 to the corners 22 of the shaft 16 contact the flats sides 9 of the socket 11. The transition region is a broad smooth surface tapering to the shaft dimension across its corners. Therefore, it tends to wedge into the socket 11. Rocking the shaft 16 from side to side helps to release the shaft 16 and allow it to seat. But, this procedure does not always work and the shaft 16 occasionally needs to be disengaged and reinserted into the socket 11. In the case of a wire driver, the shaft 16 is enclosed in the tool head 10 and is mounted on free wheeling bearings 26. Rotating the tool head 10 about the shaft axis does not tend to free a wedged shaft 16 because the shaft 16 turns within the tool head 10.

Figure 13:
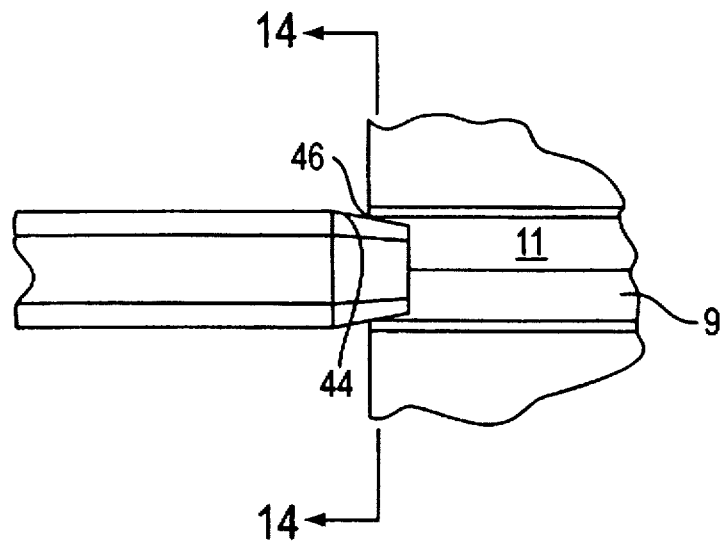
FIG. 13 is a front plan view that is partially sectioned to show the interaction between the insertion end of the shaft of FIG. 10 with the socket of the handpiece of FIG. 3.
Figure 14:
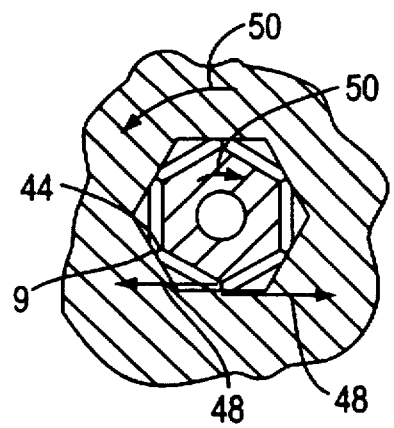
FIG. 14 is a diagram depicting the resultant forces created by the interaction shown in FIG. 13.

FIGS. 9–12 depict a preferred embodiment of the present invention. This preferred assembly is also depicted in the exemplary tool head and rotary hand piece shown in FIGS. 2–6. A shaft assembly 30 includes a shaft 32 having a longitudinal axis. The shaft 32 has a polygonal cross sectional shape perpendicular to the longitudinal axis. The shaft 32 includes a plurality of sides 34 with adjacent sides meeting at corners 36. The shape of the shaft 32 corresponds to the socket 11 so that they positively engage to transmit torque. The exemplary shaft 16 and socket 11 have a hexagonal shape. The shaft 32 is mounted on bearings 38 within tool head 10. The shaft has an insertion end 40. In the wire driver depicted, the shaft 32 is exposed from the tool head at its insertion end 40. The insertion end 40 includes a plurality of converging planar surfaces 42 formed for example by belt grinding or by milling. There is a one-to-one correspondence between the sides of the shaft polygon 34 and the converging planar surfaces 42 so that a cross section of the tapered end 40 perpendicular to the longitudinal axis is also a polygon having the same number of sides as the shaft polygon but having a smaller area. The corners 36 of the shaft polygon continue along the tapered end 40 to form corners 44 on the tapered end 40. When the tapered end 40 is inserted into the socket 11 the corners 44 of the tapered end 40 contact the sides 9 of the socket 11. The corners 44 are lines formed by the intersections of planar surfaces 42. Furthermore, the corners 44 converge from a maximum spacing adjacent the shaft 32 to a minimum spacing adjacent the free end of the shaft. This insertion end geometry results in point contact 46 between the sides 9 of the socket 11 and corners 44 of the insertion end 40 as shown in FIG. 13. The tapering corners 44 combined with axial force pushing the shaft 32 into the socket 11 creates lateral resultant forces 48 between the corners 44 and the sides 9 as shown in FIG. 14. The lateral resultant forces 48 act across the radius of the shaft 32 and socket 11 to generate resultant torsional forces 50 that cause the shaft 32 and socket 11 to rotate into alignment with one another. This shaft and socket arrangement will be self-aligning unless the corners 44 contact the sides 9 exactly in the centers of the sides 9 so that no lateral resultant forces arise. If this occurs, slight rocking of the tool head is sufficient to change the orientation of the point contact 46 so that it is beneficially unstable and generates the self-aligning resultant forces.

The present invention as depicted in FIGS. 9–12 also provides an improved collet that prevents misalignment of wires or shafts placed in the collet. The shaft 32 has a collet end 52. A plurality of tangs 54, four in this exemplary embodiment, are formed from the shaft 32 wall. The tangs are separated by nonlinear slots 56 in the shaft 32 wall. The embodiment of FIGS. 9–12 has zig-zag shaped slots 56. The four slots shown can be formed by cutting opposite slots simultaneously as the cutting tool, the part, or both are moved. The part can then be turned and the other pair of slots formed. If an odd number of slots or irregular spacing of slots is desired they can be cut individually. This type of slot can be produced by relative side-to-side motion or by relative alternating rotational motion. The intersection of the slots 56 forms a central bore along the longitudinal axis. Alternatively, the shaft may have a bore formed along the longitudinal axis, such as by drilling, that is larger than the intersection of the slots 56 in order to accommodate a larger wire or shaft. A wire 58 or shaft inserted between the tangs 54 is guided along the longitudinal axis and contained in the center of the tangs 54. The wire 58 or shaft is prevented from protruding between the tangs by the non-linear slots 56. If the wire 58 or shaft is directed against the inside of the tangs, the wire is not presented with any opening parallel with the longitudinal axis that is sufficiently long to allow the wire 58 or shaft to slip between the tangs 54. In the exemplary wire driver arrangement, the shaft assembly 30 is mounted in a housing 57. An end cap 59 threads onto the housing 57 and covers the collet end 52. A tapered portion 61 of the end cap 59 cooperates with a tapered portion 63 of the collet end 52 to press the tangs 54 together to grip a wire when the portion 63 is advanced into portion 61. A lever 65 is actuated to move the portions 61 and 63 relative to one another. The lever moves the entire shaft assembly 30 forward in the housing 57. A spring 67 biases the shaft assembly 30 backward in the housing 57.

Figure 15:
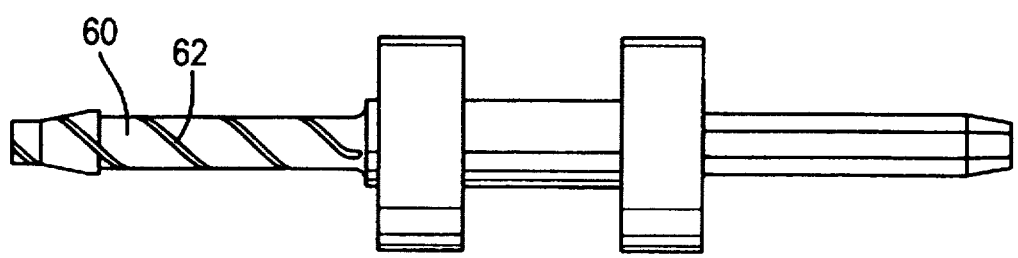
FIG. 15 is a side plan view of another alternative embodiment of a shaft assembly.

FIG. 15 depicts an alternative embodiment in which the tangs 60 are separated by non-linear spiral slots 62. This collet could be used with only two tangs 60 separated by a spiral slot 62. Likewise it could have multiple tangs and slots like the embodiment of FIG. 9. The spiral slots 62 of this embodiment can be produced by continuous relative rotation as the part or cutting tool is advanced.

It will be understood by those skilled in the art that the foregoing has described a preferred embodiment of the present invention by way of an exemplary modular wire driver assembly. The invention can be used to provide an improved shaft insertion end geometry in a modular tool head that does not have a collet end. Likewise, the improved shaft collet end can be used in a non-modular tool head. Finally, additional variations in design and construction may be made to the preferred embodiment without departing from the spirit and scope of the invention defined by the appended claims.

What is claimed is:

1. A rotary drive handpiece and modular tool head, the modular tool head being releasably engageable with the handpiece, a drive mechanism for transmitting torque from the handpiece to the tool head, the drive mechanism comprising a socket and corresponding mating shaft having a longitudinal axis, the shaft having a polygonal cross-sectional shape perpendicular to the longitudinal axis, the socket having a corresponding polygonal shape such that the shaft positively engages the socket, the polygon being multi-sided, the sides of the polygon meeting at a corner between each adjacent pair of sides, one end of the shaft being tapered.

2. The rotary drive handpiece and modular tool head of claim 1 wherein the tapered end of the shaft is a frustoconical taper that blends with the polygonal shaft.

3. The rotary drive handpiece and modular tool head of claim 1 wherein the tapered end includes a plurality of converging planar surfaces, there being a one-to-one correspondence between the sides of the shaft polygon and the converging planar surfaces so that a cross section of the tapered end perpendicular to the longitudinal axis is also a polygon having the same number of sides as the shaft polygon but having a smaller area, the corners of the shaft polygon continuing along the tapered end so that when the tapered end is inserted into the socket the corners of the tapered end contact the sides of the socket causing the shaft and socket to rotate into alignment with one another.

4. A modular tool head for use with a rotary drive handpiece having a handpiece socket, the handpiece socket being a multi-sided polygonal shape wherein adjacent sides of the polygon meet at corners, the tool head comprising:

a shaft having a longitudinal axis and an insertion end adapted for insertion into the socket, the shaft having a polygonal cross-sectional shape corresponding to the shape of the socket, the insertion end of the shaft including a plurality of converging planar surfaces, there being a one-to-one correspondence between the sides of the shaft polygon and the converging planar surfaces so that a cross section of the insertion end perpendicular to the longitudinal axis is also a polygon having the same number of sides as the shaft polygon but having a smaller area, the corners of the shaft polygon continuing along the insertion end so that when the tapered end is inserted into the socket the corners contact the sides of the socket causing the shaft and socket to rotate into alignment with one another.

5. The modular tool head of claim 4 wherein the shaft further comprises a collet end opposite the insertion end, the collet end having a shaft wall, the shaft wall being divided by non-linear grooves to form a plurality of tangs generally parallel to the longitudinal axis.

6. The modular tool head of claim 5 wherein the non-linear grooves are zig-zag shaped.

7. The modular tool head of claim 5 wherein the non-linear grooves spiral about the longitudinal axis.

8. A tool head for a rotary handpiece, the tool head having a shaft comprising a shaft wall oriented along a longitudinal axis, the shaft having a collet end having a plurality of tangs generally parallel to the longitudinal axis, the tangs being separated from one another along their length by non-linear grooves formed in the shaft wall.

9. The modular tool head of claim 8 wherein the non-linear grooves are zig-zag shaped.

10. The modular tool head of claim 8 wherein the non-linear grooves spiral about the longitudinal axis.

11. The modular tool head of claim 8 wherein the shaft further comprises an insertion end opposite the collet end, the insertion end of the shaft having a multi-sided polygonal shape wherein adjacent sides of the polygon meet at corners, the insertion end including a plurality of converging planar surfaces, there being a one-to-one correspondence between the sides of the shaft and the converging planar surfaces so that a cross section of the insertion end perpendicular to the longitudinal axis is also a polygon having the same number of sides as the shaft polygon but having a smaller area, the corners of the shaft polygon continuing along the insertion end.

* * * * *